United States Patent
Grandadam

[11] 3,939,265
[45] Feb. 17, 1976

[54] NOVEL ZOOTECHNICAL COMPOSITIONS

[76] Inventor: Jean André Grandadam, 4, Rue Lhomme, 94100 Saint-Maur Des Fosses, France

[22] Filed: Jan. 16, 1975

[21] Appl. No.: 541,387

Related U.S. Application Data

[63] Continuation-in-part of Ser. No. 356,495, May 2, 1973, abandoned.

[30] Foreign Application Priority Data

May 10, 1972 France .......................... 72.16665
Sept. 14, 1973 France .......................... 73.33060

[52] U.S. Cl. ......... 424/239; 260/397.45; 260/397.5
[51] Int. Cl.² ........................................ A61K 31/56
[58] Field of Search ....................... 424/239, 241

Primary Examiner—Elbert L. Roberts
Attorney, Agent, or Firm—Hammond & Littell

[57] ABSTRACT

Novel zootechnical compositions and a method of upgrading of domestic animals such as cattle by administering under the skin of cattle a mixture of an anabolisant steroid of the formula

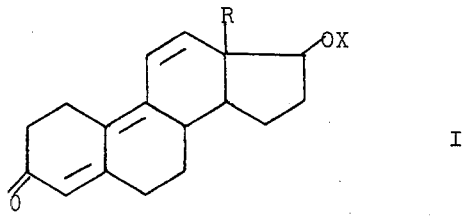

I wherein R is alkyl of 1 to 4 carbon atoms and X is selected from the group consisting of hydrogen, lower alkyl optionally substituted with phenyl, lower alkenyl, lower alkoxy-lower alkyl, lower alkyl-thialower alkyl, cycloalkyl of 3 to 7 carbon atoms, cycloalkyl lower alkyl, heterocycloalkyl, cyclic alkyl wherein the ring is derived from an unsaturated nitrogen, oxygen or sulfur heterocycle of 5 to 7 carbon atoms and acyl of an organic carboxylic or carbonic acid of 1 to 18 carbon atoms and an estrogenic steroid of the formula

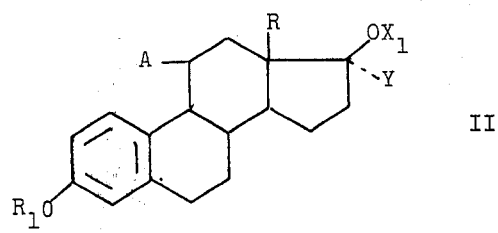

II wherein R is alkyl of 1 to 4 carbon atoms, $R_1$ is selected from the group consisting of hydrogen, alkyl of 1 to 5 carbon atoms and cycloalkyl of 3 to 7 carbon atoms, A is selected from the group consisting of hydrogen and β-alkoxy of 1 to 4 carbon atoms, Y is selected from the group consisting of hydrogen, methyl, ethynyl and haloethynyl and $X_1$ is selected from the group consisting of hydrogen and acyl of an organic carboxylic or carbonic aliphatic or cyclanic acid of 1 to 10 carbon atoms.

16 Claims, No Drawings

NOVEL ZOOTECHNICAL COMPOSITIONS

PRIOR APPLICATION

This application is a continuation-in-part of copending, commonly assigned U.S. patent application Ser. No. 356,495 filed May 2, 1973, now abandoned.

STATE OF THE ART

German Pat. No. 1,047,596 describes cattle feed containing an estrogenic compound and testosterone or a testosterone derivative (essentially androgenic products) but there is no suggestion therein of using an anabolisant agent. Canadian Pat. No. 889,253 describe compositions for the breeding of pigs based on methyltestosterone and diethylstilbestrol which are susceptible of leaving hormonal substances in organs of the animals notably diethylstilbestrol whose digestive metabolism is complex and whose elimination is slow. For this reason, there is a fear that the active principles with a hormonal action can be found in the slaughtered animals which can be absorbed by the consumer.

OBJECTS OF THE INVENTION

It is an object of the invention to provide novel zootechnical compositions for increasing the weight of breeding animals.

It is another object of the invention to provide a novel method of increasing the weight and upgrading the meat of farm animals such as pigs and cows.

These and other objects and advantages of the invention will become obvious from the following detailed description.

THE INVENTION

The novel compositions of the invention are comprised of a mixture of an anabolisant steroid of the formula

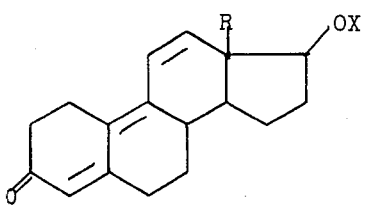

I wherein R is alkyl of 1 to 4 carbon atoms and X is selected from the group consisting of hydrogen, lower alkyl optionally substituted with phenyl, lower alkenyl, lower alkoxy-lower alkyl, lower alkyl-thialower alkyl, cycloalkyl of 3 to 7 carbon atoms, cycloalkyl lower alkyl, heterocycloalkyl, cyclic alkyl wherein the ring is derived from an unsaturated nitrogen, oxygen or sulfur heterocycle of 5 to 7 carbon atoms and acyl of an organic carboxylic or carbonic acid of 1 to 18 carbon atoms and an estrogenic steroid of the formula

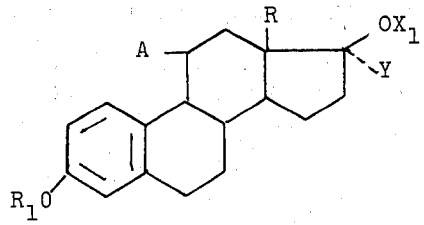

II wherein R is alkyl of 1 to 4 carbon atoms, $R_1$ is selected from the group consisting of hydrogen, alkyl of 1 to 5 carbon atoms and cycloalkyl of 3 to 7 carbon atoms, A is selected from the group consisting of hydrogen and $\beta$-alkoxy of 1 to 4 carbon atoms, Y is selected from the group consisting of hydrogen, methyl, ethynyl and haloethynyl and $X_1$ is selected from the group consisting of hydrogen and acyl of an organic carboxylic or carbonic aliphatic or cyclanic acid of 1 to 10 carbon atoms.

Preferred compositions comprise a mixture of 17$\beta$-acetoxy-$\Delta^{4,9,11}$-estratriene-3-one or 17$\beta$-amyloxy-$\Delta^{4,9,11}$-estratriene-3-one or 17$\beta$-hexahydrobenzyloxycarbonyloxy-$\Delta^{4,9,11}$-estratriene-3-one as the anabolisant and estradiol as the estrogen in the form of an implant for placement under the skin of the animals. The compositions of the invention do not cause any hormonal disturbance in the animals being raised while permitting a rapid rise in weight and an improvement in the quality of meat.

The compositions of the invention are not capable of leaving hormonal products in the organs of the animals which effect could be harmful to the consumer. It is particularly useful to employ an estrogen with a structure analogous or identical to natural hormones to assure a more regular metabolism and a more complete elimination. At the time of slaughter, the total disappearance of the active principle at the point of deposit is verified. Finally, the simultaneous presence of the 2 active principles reenforce the favorable action against the increase of one and the other so that the result is a sensibly greater weight gain.

According to another characteristic of the invention, the compositions permit besides other active principles intervening to minimize the hormonal effects of the estrogen substance and/or increase the resorption of the compositions. Among the compounds for minimizing the hormonal effects of estrogen are progestatives such as progesterone, 19-nor-progesterone, 17$\alpha$-acetoxy-6$\alpha$-methyl-pregnane-3,20-dione or 17$\alpha$-methyl-19-nor-$\Delta^{4,9}$-pregnadiene-3,20-dione which can be added to the compositions.

Among the compounds for increasing the resorption of the compositions in the case of implantation notably, the anti-inflammatory agents can be cited, particularly cortisonic compounds. It is understood that a compound possessing the anti-inflammatory properties of cortisone are characterized by a steroid structure having a 3-keto group, a hydroxy or keto group in the 11-position, a free or esterified ketolic chain in the 17β-position, a hydrogen or hydroxy in the 17α-position and 1 or 2 double bonds in the A ring. The rings can also have other substituents such as chlorine or fluorine in the 4-position, methyl, trifluoromethyl or halogen such as fluorine in the 6-position, a halogen such as fluorine in the 9-position, a methyl in the 16α or 16β-position, or methylene in the 16-position or methylene or difluoromethylene in 6,7-position. The preferred cortisonic steroid is 21-(β-ethoxy-β-ethoxy)-ethoxyacetate of dexamethasone.

A modification of the invention therefore consists of a composition containing an anabolisant steroid, an estrogenic steroid, a progestative compound and/or a cortisonic steroid. The preferred compositions are an anabolisant steroid, an estrogenic steroid, progesterone and/or 21-(β-ethoxy-β-ethoxy)-ethoxyacetate of dexamethasone.

The novel method of increasing the weight of farm animals, particularly pigs and cows, comprising administering to farm animals an effective amount of a composition consisting of an anabolisant steroid and an estrogenic steroid. The compositions are usually administered to cows, particularly calves, as an implant under the skin, preferably in the ear lobe or the skin folds near the ear. However, the compositions can also be deposited in the neck of the animal or the fessier muscle. Instead of implants, the compositions can be injected in the form of a suspension or solution. The implants, however, have the advantage that the resorption is slower but more complete.

After about 61 days, the resorption of the implants is at least 30% and the resorption of the active principle contained therein is sensibly more important and is of the order of 50%. After 3 months, the resorption of the implants is generally complete and each of the active principles has disappeared in a practically complete manner at the point of implantation as well as in the rest of the organism.

In the case of an excipient containing sodium glycolate of starch, the resorption is more rapid and is generally more complete also. The resorption is complete in about 45 days in this case.

The amount of the composition to be administered depends largely on the species of animal being treated and the method of administration. In the raising of cows, particularly calves, the compositions may contain 1 to 300 mg of a anabolisant steroid, 0.05 to 50 mg of an estrogenic steroid. The compositions may also contain 1 to 300 mg of a progestative and 0.05 to 5 mg of a cortisonic steroid for implants. The particular strength is largely dependent upon the intensity of the effect of each component of the implants desired.

The compounds of formulae I and II used in the zootechnical compositions of the invention are well known in the art. See for example, Volumes I and II of Steroid Drugs by Applezweig and French Pat. Nos. 1,380,414; 1,492,985; 1,540,942; 1,514,122; 1,476,509 and 1,514,082.

In the following examples there are described several preferred embodiments to illustrate the invention. However, it should be understood that the invention is not intended to be limited to the specific embodiments.

EXAMPLE 1

An implant containing an estrogenic steroid and an anabolisant steroid was prepared from 140 mg of 17β-acetoxy-$\Delta^{4,9,11}$-estratriene-3-one and 20 mg of estradiol and sufficient lactose base to make a tablet.

A similar implant was prepared from 140 mg of 17β-acetoxy-$\Delta^{4,9,11}$-estratriene-3-one, 20 mg of estradiol and a mixture of sodium glycolate of starch, polyvinylpyrrolidone and magnesium stearate to make a final tablet weighing 165 mg.

An implant containing a progestative, an estrogen and an anabolisant was prepared from 140 mg of 17β-acetoxy-$\Delta^{4,9,11}$-estratriene-3-one, 20 mg of estradiol, 200 mg of progesterone and a lactose excipient. A similar implant also containing an anti-inflammatory agent was prepared from 140 mg of 17β-acetoxy-$\Delta^{4,9,11}$-estratriene-3-one, 20 mg of estradiol, 200 mg of progesterone, 0.35 mg of 21-(β-ethoxy-β-ethoxy)-ethoxy acetate of dexamethasone and a lactose excipient.

EFFECT OF IMPLANTS ON CATTLE

The influence on zootechnical performances was determined on four groups of male Pie black calves weighing between 56 and 60 Kg. One group was the control, one group received an implant of a tablet containing 20 mg of estradiol and 200 mg of progesterone (implant I), one group received an implant of a tablet containing 20 mg of estradiol, 200 mg of progesterone and 140 mg of 17β-acetoxy-$\Delta^{4,9,11}$-estratriene-3-one (implant II) and the fourth group received an implant containing 20 mg of estradiol, 200 mg of progesterone, 140 mg of 17β-acetoxy-$\Delta^{4,9,11}$-estratriene-3-one and 350γ of 21-(β-ethoxy-β-ethoxy)-ethoxyacetate of dexamethasone (implant III). The implants were introduced in the fold of the back skin of the ear and the weight of the animals was determined at the start of the test and 34 and 61 days after implantation. The results are reported in Table I.

TABLE I

| | Controls | Implant I | Implant II | Implant III |
|---|---|---|---|---|
| Days after implantation | 61 | 61 | 61 | 61 |
| Average weight at start in Kg | 60.18 | 56.86 | 58.96 | 58.51 |
| Average weight at end in Kg | 123.67 | 124.1 | 129.60 | 131.0 |
| Weight gain at 34th day in Kg | 35.87 | 38.12 | 41.58 | 41.36 |
| Average daily weight gain at 34th day in Kg | 1.055 | 1.121 | 1.223 | 1.216 |
| Weight gain in 61 days in Kg | 63.49 | 67.24 | 70.64 | 72.49 |
| Average daily weight gain in Kg | 1.041 | 1.102 | 1.158 | 1.188 |

In another test, the calves received an implant of 165 mg pellets consisting of 20 mg of estradiol and 140 mg of 17β-acetoxy-$\Delta^{4,9,11}$-estratriene-3-one and an excipient consisting of magnesium stearate, polyvinylpyrrolidone and sodium glycolate of starch and the animals were slaughtered 42 days after the implantations. The live weight of the animals at the start and end of the test and the weight of the carcasses was determined. The carcasses were classified by the following criteria; conformation on a scale of 1 to 3, color on a scale of 1 to 3 and state of fattening on a scale of 1 to 3. The results are reported in Tables II and III.

TABLE II - TREATED ANIMALS

| No. of animals | Starting Weight in Kg | Final Weight in Kg | Weight of Carcasses in Kg | conformation + fattening + color (Total of 9) |
|---|---|---|---|---|
| 54 | 43 | 149.2 | 95 | 9 |
| 58 | 43 | 152.8 | 97 | 9 |
| 73 | 45 | 163.2 | 106 | 9 |
| 74 | 45 | 153.6 | 95 | 8 |
| 76 | 40 | 153 | 100 | 9 |
| 83 | 40 | 158.4 | 104 | 9 |
| 87 | 43.6 | 151 | 96 | 7 |
| 90 | 42.2 | 131 | 85 | 7 |
| 93 | 42 | 151.8 | 96 | 6 |
| Average | 42.64 | 151.55 | 97.11 | 8.11 |

TABLE III - CONTROLS

| No. of animals | Starting Weight in Kg | Final Weight in Kg | Weight of Carcasses in Kg | conformation + fattening + color (Total of 9) |
|---|---|---|---|---|
| 61 | 43.2 | 138 | 91 | 6 |
| 64 | 40 | 147.2 | 92 | 7 |
| 65 | 40 | 140.8 | 90 | 7 |
| 69 | 41 | 146.8 | 94 | 8 |
| 75 | 49 | 148.4 | 93 | 7 |
| 78 | 42.4 | 150 | 97 | 5 |
| 82 | 44.2 | 150 | 95 | 7 |
| 88 | 40 | 131.4 | 83 | 5 |
| 94 | 42 | 140.4 | 90 | 9 |
| 56 | 43 | 162 | 96 | 6 |
| Average | 42.48 | 145.5 | 92.1 | 6.7 |

Tables II and III shows that the weight of the treated animals is clearly greater than that of the control animals and the last column of the Tables show a note of commercial appreciation which represents an important criteria to animal buyers. Clearly the treated animals were superior to the controls.

Possible metaplasia modifications of the prostate of calves is provoked by administration of estrogens. Four groups of immature male calves were used in the test with one group serving as controls not receiving an implant (I), another group receiving an implant containing 20 mg of estradiol (II), another receiving an implant of 20 mg of estradiol and 40 mg of $17\beta$-acetoxy-$\Delta^{4,9,11}$-estratriene-3-one (III) and a last group receiving an implant containing 20 mg of estradiol and 140 mg of $17\beta$-acetoxy-$\Delta^{4,9,11}$-estratriene-3-one (IV). The implants were administered subcutaneously and the animals were slaughtered 90 days later. The results are reported in Table IV with an absence of metaplasia noted by 0 and the pluses indicating a conventional scale of metaplasia intensity.

TABLE IV

| Groups | No. of Animals | Prostatic Metaplasia | Groups | No. of Animals | Prostatic Metaplasia |
|---|---|---|---|---|---|
| I | 042 | 0 | | 016 | + |
| | 040 | 0 | | 037 | + |
| | 045 | 0 | | 030 | + |
| | 029 | 0 | | 018 | + |
| | 675 | 0 | | 019 | + |
| | 671 | 0 | | 667 | 0 |
| | 673 | 0 | III | 662 | + |
| | 099 | 0 | | 650 | +++ |
| | 678 | 0 | | 670 | + |
| | 684 | 0 | | 661 | 0 |
| | 685 | 0 | | 666 | + |
| | 674 | 0 | | 639 | 0 |
| | | | | 660 | + |
| | 649 | +++ | | 659 | 0 |
| | 669 | +++ | | | |
| | 654 | +++ | | 037 | 0 |

TABLE IV-continued

| Groups | No. of Animals | Prostatic Metaplasia | Groups | No. of Animals | Prostatic Metaplasia |
|---|---|---|---|---|---|
| II | 059 | +++ | | 047 | 0 |
| | 050 | +++ | | 627 | 0 |
| | 034 | +++ | IV | 098 | 0 |
| | 048 | +++ | | 640 | 0 |
| | 060 | +++ | | 630 | 0 |
| | 042 | +++ | | 637 | 0 |
| | | | | 634 | 0 |

Table IV shows that the animals treated with estradiol alone presented a pronounced prostatic metaplasia while group III presented a less pronounced prostatic metaplasia and group IV did not present any prostatic metaplasia. The hormonal effects of estradiol were completely annuled.

EXAMPLE 2

$17\beta$-amyloxy-$\Delta^{4,9,11}$-estratriene-3-one 22.5 Ml of dimethylsulfoxide were added to 4.5 g of sodium hydride in a 50% oil suspension in 90 ml of tetrahydrofuran and the resulting mixture was stirred for 30 minutes at 22°C. Then, 3 g of 3-ethylenedioxy-$\Delta^{4,9,11}$-estratriene-17$\beta$ol were added thereto all at once and after stirring the mixture for 30 minutes at 22°C, 6 ml of iodopentane were added thereto all at once. The mixture was stirred for 17 hours at 22°C and then 60 ml of water were added dropwise. The mixture was extracted with methylene chloride and the extracts were washed with water, dried and evaporated to dryness to obtain 4.3 g of a resin which was used as is for the next step.

The 4.3 g of the said resin were dissolved in 80 ml of tetrahydrofuran and 40 ml of 50% acetic acid in water and the resulting solution was stirred for 1 hour. The solution was poured into water and the mixture was neutralized with sodium bicarbonate addition. The mixture was extracted with methylene chloride and the extracts were washed with water, dried and distilled to dryness to obtain 6.5 g of an oil. The oil was chromatographed over silica and was eluted with isopropyl ether to obtain 1.512 g of $17\beta$-amyloxy-$\Delta^{4,9,11}$-estratriene-3-one.

$17\beta$-hexahydrobenzyloxycarbonyloxy-$\Delta^{4,9,11}$-estratriene-3-one was prepared as in French Pat. No. 5979M by reacting hexahydrobenzyl chloroformate and $\Delta^{4,9,11}$-estratriene-17$\beta$-ol-3-one.

The influence on zootechnical performances was determined in another test on groups of male Pie black calves weighing about 40 kg. One group was the control and the second group received an implant I of a tablet containing 20 mg of estradiol and 140 mg of $17\beta$-n-amyloxy-$\Delta^{4,9,11}$-estratriene-3-one and a third group received an implant II of a tablet containing 20 mg of estradiol and 140 mg of $17\beta$-hexahydrobenzyloxycarbonyloxy-$\Delta^{4,9,11}$-estratriene-3-one. The implants were introduced into the fold of the back skin of the ear and the weight of the animals was determined at the start of the test and 55 days after implantation. The yields were expressed as the ratio of the weight of the carcass to the total weight of the animal and the consumption indice is the ratio of the total weight of feed that the animal received to total weight gain. In addition, the carcasses were rated by the following 3 criteria: 1. color, 2. fattening state and 3. conformation, each on a scale of 1 to 3 with 1 being the maximum rating. The results are reported in Table V.

TABLE V

|  | Controls | Implant I | Implant II |
|---|---|---|---|
| Starting weight in Kg | 39.44 | 39.64 | 39.46 |
| Weight in Kg before implantation | 78.57 | 78.57 | 78.5 |
| Weight gain in Kg before treatment | 39.13 | 38.93 | 39.04 |
| Weight in Kg at end of test | 148 | 155 | 150 |
| Total weight gain in Kg | 108.56 | 115.36 | 110.54 |
| Daily weight gain in Kg | 0.906 | 0.961 | 0.921 |
| Weight of carcass in Kg | 92.71 | 98.14 | 95.68 |
| Yield | 62.62 | 63.29 | 63.77 |
| Color 1 | 5/14 | 4/14 | 6/14 |
| 2 | 9/14 | 9/14 | 8/14 |
| 3 | 0/14 | 1/14 | 0/14 |
| Conformation 1 | 3/14 | 13/14 | 10/14 |
| 2 | 5/14 | 0/14 | 2/14 |
| 3 | 6/14 | 1/14 | 2/14 |
| Fattening state 1 | 12/14 | 13/14 | 14/14 |
| 2 | 2/14 | 1/14 | 0/14 |
| 3 | 0/14 | 0/14 | 0/14 |
| Indice of consumption | 1.69 | 1.61 | 1.67 |

The results of Table V show that the treated animals have a much greater weight gain than the controls, both in the live animals and the carcasses of the slaughtered animals. The yield was higher as well as the conformation and fattening state and the indice of consumption was lower for the treated animals.

In another test, groups of immature male calves were used to determine possible histological modifications of the prostate. One group acted as controls and received no implant, a second group received an implant of 20 mg of estradiol and a third group received an implant III of 20 mg of estradiol and 140 mg of 17β-n-amyloxy-Δ$^{4,9,11}$-estratriene-3-one and a fourth group received an implant IV of 20 mg of estradiol and 140 mg of 17β-hexahydrobenzyloxycarbonyloxy-Δ$^{4,9,11}$-estratriene-3-one. The implants were administered subcutaneously and the animals were slaughtered 90 days later. The animals receiving the implant of estradiol alone showed a pronounced prostatic metaplasia while those receiving the implants III and IV of the invention did not present any prostatic metaplasia which indicates that the hormonal effects of estradiol were nullified in the compositions of the invention.

The results presented above show a significant increase in weight gain and upgrading of the quality of meat with the invention as compared to the controls.

The following test was conducted to compare a composition consisting of 20 mg of estradiol and 200 mg of testosterone (implant A) with a composition of the invention consisting of 20 mg of estradiol and 140 mg of 17β-acetoxy-Δ$^{4,9,11\text{-}estratriene}$-3-one (implant B). The implants were given to female Normandy calves 72 days before slaughter and were introduced into the fold of the back skin of the ear. The weight of the animals was ascertained at the start and just before slaughter and the results are reported in Table VI.

TABLE VI

| Treatment | Implant A | Implant B |
|---|---|---|
| No. of animals | 9 | 13 |
| Duration of fattening time in days | 107 | 107 |
| Average weight at start of test in Kg | 48.55 ± 1.31 | 49.00 ± 0.75 |
| Average weight at end of test in Kg | 156.89 ± 4.07 | 173.85 ± 2.172 |
| Average weight gain in Kg | 108.34 ± 3.85 | 124.85 ± 2.13 |
| Average daily weight gain in Kg | 1.012 ± 0.036 | 1.167 ± 0.02 |
| Weight of cold carcasses in Kg | 100.88 ± 2.65 | 110.21 ± 1.69 |

The results of Table VI show that the weight gain is substantially higher with implant B of the invention than with implant A of German Pat. No. 1,047,596.

It can be seen that implant B resulted in an increase in weight approximately 15% greater than that of implant A in the animals before slaughter and to about a 10% difference in the weight of the carcasses of the slaughtered animals which is extremely significant.

Various modifications of the compositions and method of the invention may be made without departing from the spirit or scope thereof and it should be understood that the invention is to be limited only as defined in the appended claims.

I claim:

1. Novel zootechnical compositions for increasing the weight of farm animals comprising a mixture of 1 to 300 mg of an anabolisant steroid of the formula

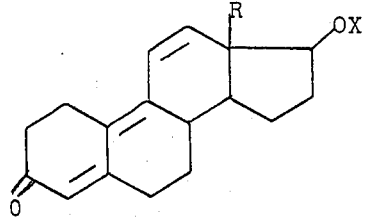

wherein R is alkyl of 1 to 4 carbon atoms and X is selected from the group consisting of hydrogen, lower alkyl optionally substituted with phenyl, lower alkenyl, lower alkoxy-lower alkyl, lower alkyl-thialower alkyl, cycloalkyl of 3 to 7 carbon atoms, cycloalkyl lower alkyl, heterocycloalkyl, cyclic alkyl wherein the ring is derived from an unsaturated nitrogen, oxygen or sulfur heterocycle of 5 to 7 carbon atoms and acyl of an organic carboxylic or carbonic acid of 1 to 18 carbon atoms and 0.05 to 50 mg of an estrogenic steroid of the formula

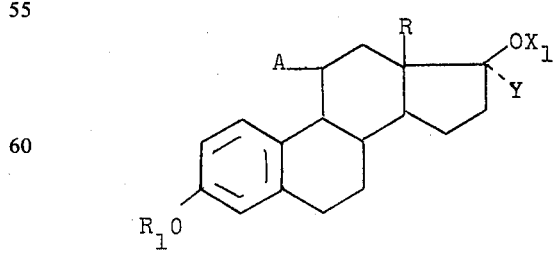

wherein R is alkyl of 1 to 4 carbon atoms, R$_1$ is selected from the group consisting of hydrogen, alkyl of 1 to 5 carbon atoms and cycloalkyl of 3 to 7 carbon atoms, A is selected from the group consisting of hydrogen and β-alkoxy of 1 to 4 carbon atoms, Y is selected from the group consisting of hydrogen, methyl, ethynyl and haloethynyl and $X_1$ is selected from the group consisting of hydrogen and acyl of an organic carboxylic or carbonic aliphatic or cyclanic acid of 1 to 10 carbon atoms.

2. A composition of claim 1 wherein the anabolisant steroid is 17β-acetoxy-$\Delta^{4,9,11}$-estratriene-3-one.

3. A composition of claim 1 wherein the estrogenic steroid is estradiol.

4. A composition of claim 1 wherein there is also a progestative compound to minimize the hormonal effects of the estrogenic steroid.

5. A composition of claim 1 wherein there is also an anti-inflammatory agent to increase the resorption of the composition.

6. A composition of claim 1 wherein the estrogenic steroid is estradiol and the anabolisant steroid is 17β-acetoxy-$\Delta^{4,9,11}$-estratriene-3-one.

7. A composition of claim 6 containing also 21-(β-ethoxy-β-ethoxy)-ethoxyacetate of dexamethasone.

8. The composition of claim 7 in the form of an implant.

9. A composition of claim 1 wherein the anabolisant steroid is 17β-amyloxy-$\Delta^{4,9,11}$estratriene-3-one.

10. A composition of claim 1 wherein the anabolisant steroid is 17β-hexahydrobenzyloxycarbonyloxy-$\Delta^{4,9,11}$-estratriene-3-one.

11. A method of improving the raising of farm animals comprising placing under the skin of farm animals a sufficient amount of a composition of claim 1 to increase the weight of the animals.

12. The method of claim 11 wherein the estrogenic steroid is estradiol and the anabolisant steroid is 17β-acetoxy-$\Delta^{4,9,11}$-estratriene-3-one.

13. The method of claim 11 wherein there is also in the composition a progestative compound.

14. The method of claim 11 wherein there is also present in the composition an anti-inflammatory agent.

15. The method of claim 11 wherein the estrogenic steroid is estradiol and the anabolisant steroid is 17β-amyloxy-$\Delta^{4,9,11}$-estratriene-3-one.

16. The method of claim 11 wherein the estrogenic steroid is estradiol and the anabolisant steroid is 17β-hexahydrobenzyloxycarbonyloxy-$\Delta^{4,9,11}$-estratriene-3-one.

* * * * *